United States Patent
Hamelmann et al.

(10) Patent No.: US 11,432,796 B2
(45) Date of Patent: Sep. 6, 2022

(54) POSITIONING SUPPORT AND FETAL HEART RATE REGISTRATION SUPPORT FOR CTG ULTRASOUND TRANSDUCERS

(71) Applicant: KONINKLIJKE PHILIPS N.V., Eindhoven (NL)

(72) Inventors: Paul Hamelmann, Aachen (DE); Lars Schmitt, Aachen (DE); Alexander Franciscus Kolen, Eindhoven (NL); Markus Wohlschlager, Sindelfingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 775 days.

(21) Appl. No.: 16/094,051

(22) PCT Filed: May 5, 2017

(86) PCT No.: PCT/EP2017/060735
§ 371 (c)(1),
(2) Date: Oct. 16, 2018

(87) PCT Pub. No.: WO2017/194392
PCT Pub. Date: Nov. 16, 2017

(65) Prior Publication Data
US 2019/0133549 A1    May 9, 2019

(30) Foreign Application Priority Data

May 12, 2016   (EP) ..................... 16169434

(51) Int. Cl.
*A61B 8/08*    (2006.01)
*A61B 8/00*    (2006.01)

(52) U.S. Cl.
CPC .......... *A61B 8/0866* (2013.01); *A61B 8/0883* (2013.01); *A61B 8/42* (2013.01);
(Continued)

(58) Field of Classification Search
None
See application file for complete search history.

(56) References Cited

U.S. PATENT DOCUMENTS 8,579,820 B2   11/2013   Jackson
9,107,584 B2    8/2015   Wohlschlager
(Continued)

FOREIGN PATENT DOCUMENTS

JP    61272035 A    12/1986
JP    8154933        6/1996
(Continued)

OTHER PUBLICATIONS

Wolfberg, "The Future of Fetal Monitoring," Rev. Obstet. Gynecol., vol. 5, No. 3-4, pp. e132-e136, 2012.
(Continued)

*Primary Examiner* — Christopher Koharski
*Assistant Examiner* — Shaheep Mohammed (57) ABSTRACT

A method for monitoring fetal health. The method of the present disclosure comprises transmitting (100) an ultrasound signal from an at least one transducer element in an array towards a maternal abdomen. An at least one ultrasonic echo signal corresponding to an at least one depth of the maternal abdomen is then received (102) by the at least one transducer element. The at least one Doppler signal is determined after the echo is received by the at least one transducer element is then processed (104) in an at least one channel. A multidimensional map is then generated (106) from the processed Doppler signal. A feedback (114) to reposition the at least one transducer element is then provided when the fetal heart is determined to lie outside an ultrasound beam volume.

20 Claims, 8 Drawing Sheets

(52) U.S. Cl.
CPC ............ *A61B 8/4245* (2013.01); *A61B 8/488* (2013.01); *A61B 8/5269* (2013.01)

(56) References Cited

U.S. PATENT DOCUMENTS

| | | |
|---|---|---|
| 2005/0251044 A1 | 11/2005 | Hoctor |
| 2007/0093702 A1 | 4/2007 | Yu |
| 2009/0204002 A1 | 8/2009 | Pandit |
| 2011/0160591 A1* | 6/2011 | Smith .................. A61B 8/0866 600/453 |
| 2013/0006111 A1* | 1/2013 | Sasaki ................ G01S 7/52074 600/441 |
| 2014/0114193 A1* | 4/2014 | Anthony ................ A61B 8/429 600/459 |
| 2014/0276070 A1* | 9/2014 | Kabakov ............ A61B 5/02411 600/453 |
| 2016/0120469 A1* | 5/2016 | Freeman .............. A61B 5/6823 600/479 |
| 2016/0157826 A1* | 6/2016 | Sisodia .................. A61B 8/461 600/454 |
| 2016/0213349 A1* | 7/2016 | Groberman .............. A61B 8/02 |

FOREIGN PATENT DOCUMENTS

| | | |
|---|---|---|
| JP | 11043186 | 2/1998 |
| JP | 2014068980 | 4/2014 |
| WO | 2007/120873 | 10/2007 |
| WO | 2015/026787 | 2/2015 |
| WO | 2017045915 | 3/2017 |

OTHER PUBLICATIONS

Voicu, et al., "New Estimators and Guidelines for Better Use of Fetal Heart Rate Estimators with Doppler Ultrasound Devices," Computational and Mathematical Methods in Medicine, vol. 2014, Article ID 784862.

Reinhard, et al., "Intrapartum signal quality with external fetal heart rate monitoring: a two way trial of external Doppler CTG ultrasound and the abdominal fetal electrocardiogram," Archives of Gynecology and Obstetrics, Nov. 2012, vol. 286, Issue 5, pp. 1103-1107.

Freeman, et al., "Fetal Heart Rate Monitoring", 4th Revise. Lippencott Williams and Wilkins, 2012, Chapter 4.

Murray, "Maternal or Fetal Heart Rate? Avoiding Intrapartum Misidentification" J Obstet. Gynecol. Neonatal Nurs., vol. 33, No. 1, pp. 93-104, 2004.

Philips Medizin Systeme Boeblingen GmbH, "Philips Addendum: Additional Information Regarding Ultrasound Fetal Monitoring," Philips Documentary, pp. 1-17, 2009.

* cited by examiner

FIG. 8

POSITIONING SUPPORT AND FETAL HEART RATE REGISTRATION SUPPORT FOR CTG ULTRASOUND TRANSDUCERS

CROSS REFERENCE TO RELATED APPLICATIONS

This application is the U.S. National Phase application under 35 U.S.C. § 371 of International Application No. PCT/EP2017/060735 filed May 5, 2017, published as WO 2017/194392 on Nov. 16, 2017, which claims the benefit of European Patent Application Number 16169434.4 filed May 12, 2016. These applications are hereby incorporated by reference herein.

BACKGROUND OF THE INVENTION

Measuring the fetal heart rate (fHR) during labor and delivery is the most commonly applied obstetric procedure to assess the health state of the fetus and to determine if early intervention is required. However, for Doppler ultrasound (US) as well as for abdominal electrodes, long periods of signal loss have been reported during fHR monitoring. For the assessment of the health state of the fetus, these long signal loss periods strongly limit the interpretation of the fHR traces in clinical practice.

The ultrasound Doppler recording quality highly depends on the correct placement of the transducer on the maternal abdomen, since the fetal heart needs to be located within the ultrasound beam. However, finding the optimal transducer position can be a challenging task. In clinical practice, skilled nurses palpate the maternal abdomen and determine the fetal presentation from the outside. By relying on a signal-quality indicator and by listening to the acoustical Doppler output of the cardiotocographic (CTG) monitoring system, the ultrasound transducer is then moved over the maternal abdomen until an acceptable signal strength is found. Sometimes obtaining a good signal is not possible, such that real time imaging techniques are required for further assistance to find the location of the fetal heart. Finding the location of the fetal heart can be especially challenging in early weeks of gestation.

In long monitoring sessions the probability that either the ultrasound transducer gets miss-positioned or the fetal heart moves out of the ultrasound beam is high. Consequently, the clinical staff needs to reposition the ultrasound transducer frequently to reacquire an accurate fHR signal.

A common problem of today's ultrasound CTG transducers is that the signal containing fetal heartbeat information represents only a portion of the entire received signal. Signal contributions from other moving structures, like maternal arteries lying behind the fetal heart, are superimposed but actually unwanted. Any signal contribution, other than the reflection from the fetal heart, reduce the accuracy of the subsequent heart beat calculation or can, at the worst, lead to a registration of the maternal signal.

In order to cover a large measurement volume and to be less prone to fetal heart displacement, the ultrasound transducer of a fetal heart rate monitor contains several sub-elements equally spaced positioned in a circular arrangement. These piezo elements are excited simultaneously, effectively forming virtual one large element and hence one large ultrasound beam. The measured Doppler signal effectively is an integration of all moving objects within the volume of observation and no spatial information can be obtained. The depth extension of the observation volume typically is chosen to be long in order to cover a large variety of body constitutions. However, this does not allow to get any depth information on the fetal heart location. In addition, the signal to noise ratio (SNR) of the received signals is reduced when the sample volume length is longer than required.

Obtaining location information of the fetal heart and other Doppler echo sources within a volume of observation, increases the robustness and usability of the ultrasonic Doppler based fHR monitoring method.

U.S. Pat. App. No. 2007/0093702 discloses an acoustic energy transducer unit where the transducer unit can be an ultrasonic array, annular array, a combination thereof, or a single element transducer. It discloses a process for non-invasive monitoring of a patient's health parameter relating to blood, such as a fetal cardiovascular system. The Doppler echo signal received by the ultrasound transducer array is used to generate a 3D volumetric image and monitor fetal heart oxygenation levels. Blood parameters are monitored by use of light radiated into the target area. The ultrasound transducer is then used to induce a change in the target area, which can be monitored by the optical sensor.

SUMMARY OF THE INVENTION

The present disclosure describes a system that overcome common problems related to fetal heart rate monitoring as part of a CTG (Cardio Toco Graphy) system based on ultrasound Doppler heart beat registration. The system uses an array of independent piezo acoustic transducers distributed on a horizontal surface, such that 3D spatial information on the location of the fetal heart can be obtained. Presenting the spatial location of the fetal heart within the volume of observation covered by the transducer can facilitate the initial placement of the transducer. Furthermore, by being able to exclude maternal arteries from the measurement volume, this will help to avoid mistakenly measuring the maternal heart rate instead of the fetal heart rate. This results in more robust recordings of fetal heart rate, allowing better assessment of fetal health status, which improves safety of the fetus.

The present disclosure relates to a method for monitoring fetal health using an ultrasound device. The method comprises: transmitting an ultrasound signal to create a measurement volume from an at least one transducer element in an array towards a maternal abdomen; receiving by the at least one transducer element an at least one ultrasound signal echo corresponding to at least one depth of the maternal abdomen; processing in an at least one channel the at least one signal echo received by the at least one transducer element to create at least one Doppler signal; generating a multidimensional map from the processed Doppler signal; and providing a feedback to reposition the at least one transducer element when the fetal heart is determined to lie outside of substantial central alignment within the measurement volume.

In some embodiments, the present disclosure include a method of monitoring fetal health including transmitting an ultrasound signal from an at least one transducer element in an array towards a maternal abdomen; receiving by the at least one transducer element an at least one ultrasound signal echo corresponding to at least one depth of the maternal abdomen; processing in an at least one channel the at least one signal echo received by the at least one transducer element to create the Doppler signal; generating a multidimensional map from the processed Doppler signal; and providing a feedback to reposition the at least one transducer element when the fetal heart is determined to lie outside an ultrasound measurement beam volume.

This method and other implementations of technology disclosed herein may each optionally include one or more of the following features.

In some implementations, the method may include determining a direction towards the fetal heart. In still other embodiments, the method may include providing a directional indication towards the fetal heart based on the determined direction towards the fetal heart. Still other implementations may include illuminating a portion of a housing or a light source connected with the housing or integrated within the housing for the at least one transducer element. In some versions, feedback includes providing visual feedback of the directional indication on a user device. In even other versions, the feedback includes haptic feedback transmitted through an ultrasound device.

Various other implementations the generating a multidimensional map is based upon the processed Doppler signals and includes generating a 3D heat map. In some versions, the 3D heat map may include measuring a plurality of Doppler signals at a plurality of sample volumes. In other versions, the measuring of the plurality of Doppler signals includes using a plurality of range gates. Still further embodiments include generating the multidimensional map from the processed Doppler signals including generating a 2D heat map integrated with a depth heat map. Still further versions may generate the multidimensional map from the processed Doppler signals which includes generating a 2D heat map and a depth heat map and presenting both the 2D heat map and the depth map on a user device. In yet other versions, it may include highlighting a portion of the depth heat map corresponding to a portion of the 2D heat map being displayed. In yet others, the method may further include automatically switching from a fetal heart rate monitoring mode to a position support mode when the fetal heart is determined to lie outside an ultrasound measurement beam volume.

In some implementations, the present disclosure may describe a method of monitoring fetal health, comprising: entering a position support mode of operation for an ultrasound device; transmitting ultrasound signals from at least one transducer of the ultrasound device to create an ultrasound beam volume; receiving by the transducer ultrasound signal echoes corresponding to a depth in a maternal abdomen; processing by a processor the received ultrasound signal echoes received by the transducer to create at least one Doppler signal; generating a multi-dimensional map from the processed at least one Doppler signal; determining from the three-dimensional map, when a fetal heart is outside of being substantially centrally aligned within the ultrasound beam volume; providing feedback on how to position the transducer such that the fetal heart lies substantially centered within the beam volume.

This method and other implementations of technology disclosed herein may each optionally include one or more of the following features.

In some implementations, the providing of feedback includes illuminating light sources on the ultrasound device. In yet other versions, the light sources indicate a direction from a center of the beam volume. In still other versions, the providing of feedback includes presenting information on a user device indicating a direction from a center of the beam volume. Some aspects may also include automatically entering a fetal heart rate mode on the ultrasound device upon determining that the fetal heart lies substantially centered within the beam volume.

In some implementations, method may include switching the ultrasound device from a fetal heart rate mode to position support mode upon detecting when the fetal heart is outside the ultrasound beam volume. Other implementations may further generate the three dimensional map from a combined construct of a two dimensional heat map and a depth heat map.

The present disclosure further describes an apparatus for measuring fetal heart rate, comprising: an ultrasonic device having a plurality of transducers, at least one processor and associated memory, wherein the memory has instructions which, when executed by the processor, configure the processor to: transmit ultrasound signals from a plurality of transducers on the ultrasound device; receive by the transducers ultrasound signal echoes corresponding to depth in a maternal abdomen; process determined Doppler signals based upon the signal echoes received by the transducers; generate a multi-dimensional map from the processed Doppler signals; determine from the three-dimensional map, when a fetal heart is substantially outside a central alignment of an ultrasound beam volume; provide feedback on how to position the ultrasound device such that the fetal heart lies substantially centered within the beam volume.

Other implementations may include a non-transitory computer readable storage medium storing instructions executable by a processor (e.g., a central processing unit (CPU) or graphics processing unit (GPU)) to perform a method such as one or more of the methods described above. Yet another implementation may include a system of one or more computers and/or one or more functional devices that include one or more processors operable to execute stored instructions to perform a method such as one or more of the methods described above.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings.

DETAILED DESCRIPTION

The following are definitions of terms as used in the various embodiments of the present disclosure.

The term "depth" as used herein refers to a distance measured from the transducer array plane to a point within the maternal abdomen volume that is being scanned. Depth is set to have a value of "0" at the inner wall of the maternal abdomen and a maximum value at the farthest point from which a Doppler signal can be obtained. The depth may be, in some embodiments, the middle of the sample volume from which the Doppler signal is calculated.

The term "channel" as used herein refers to a wired or wireless data pathway allocated to each transducer element in a transducer array disclosed in the present disclosure. One channel is set aside for processing the Doppler signal received from all transducer elements when the ultrasound device is used in the fetal heart rate mode (fUR-mode).

The term "feedback" as used herein refers to an audio, visual, or combined audio and visual signal indicative of a received Doppler signal quality.

The term "heat map" as used herein refers to graphical representation of the Doppler signal received by the transducer array, wherein different colors correspond to different values of the Doppler signal strength.

The term "transducer" as used herein refers to the ultrasound device component that is used to probe the fetal heart.

The present disclosure relates to a method for monitoring fetal health using an ultrasound device. The method comprises: transmitting an ultrasound signal from an at least one transducer element in an array towards a maternal abdomen; receiving by the at least one transducer element an at least one Doppler signal corresponding to at least one depth of the maternal abdomen; transmitting via an at least one channel the at least one Doppler signal received by the at least one transducer element; processing the at least one Doppler signal received by the at least one transducer element; generating a multidimensional map from the processed Doppler signal; providing a feedback to reposition the at least one transducer element when the fetal heart is determined to lie outside an ultrasound beam volume.

Figure 1:
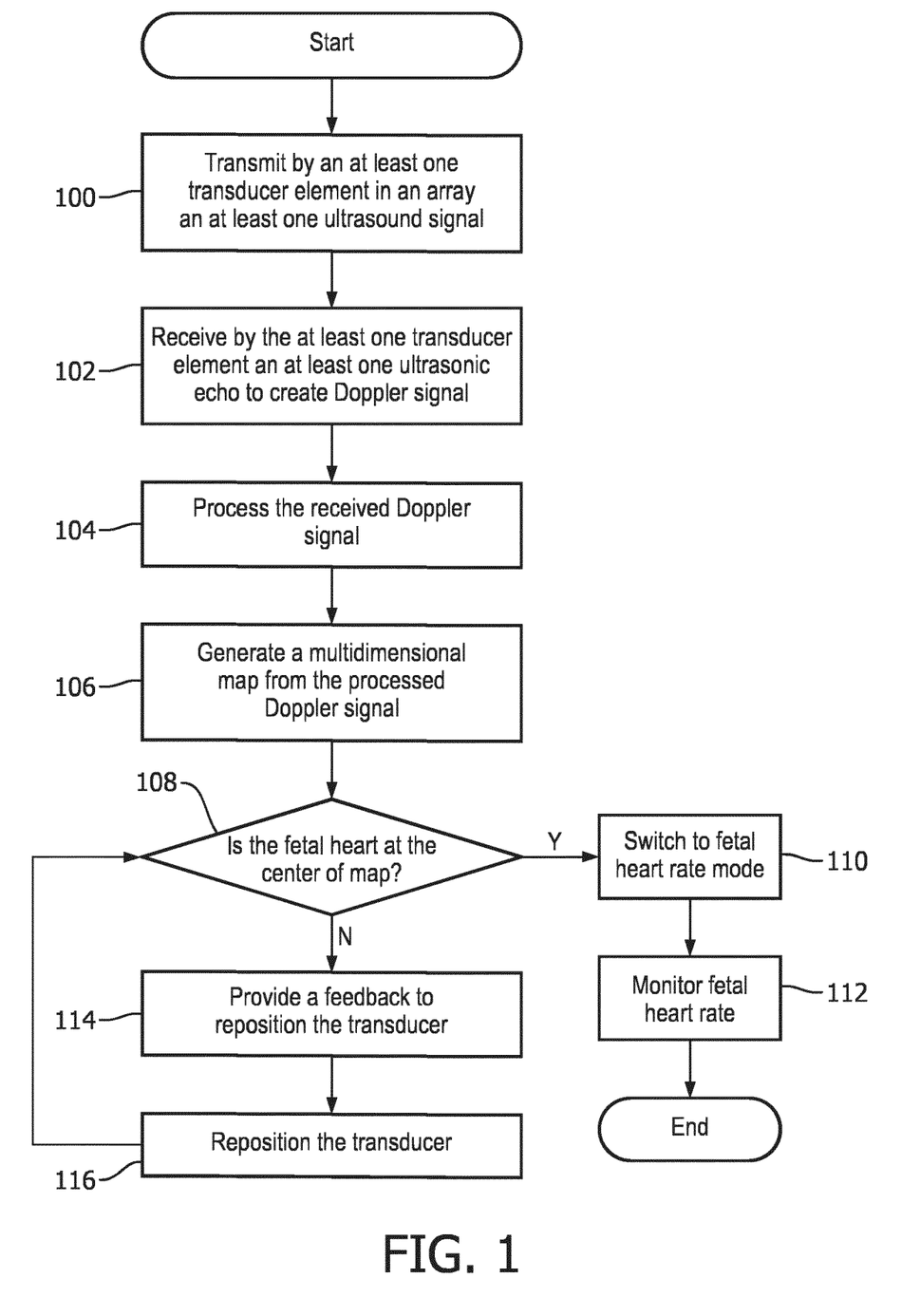
FIG. 1 is a flowchart illustrating a method for determining an optimal position of an ultrasound transducer during fetal health monitoring, herein referred to as position support mode (PS-mode) of the ultrasound device, according to an embodiment of the present invention.

FIG. 1 is a flowchart illustrating a method for determining an optimal position of an ultrasound transducer during fetal health monitoring, herein referred to as position support mode (PS-mode) of the ultrasound device, according to an embodiment. In this mode, the ultrasound device transmits an at least one ultrasound signal via an at least one transducer element in a transducer array (step 100) positioned against a maternal abdomen. The transducer elements are preferably arranged in a ring such that one transducer element is located at the center of the said transducer array, and additional transducer elements are located in the periphery. In an embodiment, the additional transducer elements are equidistant from the center and equally spaced from each other.

To make an unambiguous determination of the fetal heart location possible, only one element of the transducer is preferably used for transmission. Following an ultrasound signal transmission, a Doppler signal is generated based upon the ultrasonic signal echo which is received by the at least one transducer element corresponding to at least one depth of the maternal abdomen (step 102). The response echo signals from each receiving element are preferably processed individually in separate channels. Based on the signal strength of these Doppler signals, the fetal heart location can be estimated. The center element may also be used to generate an Ultrasound wave burst. Using only one driving element has the advantage that the location of the fetal heart can be determined unambiguously.

During the receive phase, all elements are used to receive the ultrasonic echo reflected by the fetal heart. The received echo signals are transmitted via at least one channel and processed (step 104) to create the Doppler signals. The received ultrasound echoes of each element are preferably processed individually. The Doppler signals are obtained in some embodiments by using a synchronous demodulation of the ultrasonic echo signals. The power of the created Doppler signals is determined wherein it may be calculated over a certain time window. The time window needs to be long enough (e.g., 1 sec) to allow for several heart beats within this period. The power received in the individual elements may be color coded visually, which provides an estimation of the fetal heart location. Each transducer element is preferably assigned a single channel, which transmits the signal via wired or wireless connection to a user device. The user device is preferably a computing device, e.g., a smartphone or a tablet. Furthermore, the fetal heart location information and transducer positioning support can also be sent to a smartphone app or a remote device.

In use, in one embodiment, the at least one transducer element receives ultrasound echoes from an at least one depth of the maternal abdomen from which the Doppler signal is created. For example, with a pulse repetition frequency of 2000 Hz, within one second the transducer elements receive two thousand ultrasound signals from which a Doppler signal of one second is created using a demodulation scheme. The Doppler signal therefore is represented by the already processed raw ultrasound data received with the transducer elements.

The power of the received Doppler signal from each individual transducer element obtained at different depths can be used to provide a 3D feedback for optimal transducer positioning (e.g., finding the strongest Doppler signal by an element in the middle of the matrix, when fixating the ultrasound transducer to the maternal abdomen). The signal strength of the Doppler signal can be color-coded and visualized on the display of the monitor. When the position support mode is active, a coarse 3D-heat map of Doppler sources in the maternal abdomen can be visualized (step 106). This allows the system to provide feedback on how to move the transducer such that the fetal heart lies substantially centered within the beam volume of observation, maternal arteries are excluded from the volume of observation, and the heart of twins are not within the same depth segment of observation. The fetal heart position is then determined relative to the center of the 2D-heat map (step 108). The device can switch between normal operation, e.g., fHR measurement mode as used in the current Philips Avalon transducer (fHR-mode) (step 110) and the described positioning support mode (PS-mode). Once in fHR-mode, the ultrasound device monitors the fetal heart rate (step 112).

On the other hand, if the fetal heart is determined to lie outside the center of the 3D-heat map, displacement of the fetal heart out of the ultrasound beam volume can be detected and visual feedback can be given (step 114) for intuitive repositioning of the transducer, possibly done by the mother herself (by activating the PS-mode), which reduces the periods of signal dropouts and eases the work of the medical staff. Also, LEDs on the housing of the transducer can provide a directional indication of which element receives the strongest Doppler signal such that the operator gets a direct visual feedback on the optimal transducer position. Alternatively, a plurality of LEDs could indicate in which direction the transducer should be moved. In another embodiment, a beeping sound is generated which will indicate when the transducer is placed at an optimal centralized position. In still other embodiments, the feedback may be in the form of an audio alert indicating the position of the transducer elements relative to the fetal heart, e.g., the audio alert's volume or frequency increases to indicate that the fetal heart is approaching the map center. Once the user receives the feedback, the transducer element is repositioned so that the fetal heart lies at the center of the 3D-heat map (step 116).

Thus, as described in the various embodiments, the device and method disclosed herein includes a number of mechanisms for providing feedback indicative to reposition the transducer/device. In various embodiments, the feedback may be visual and be provided directly from the transducer housing. In still other variations and implementations, the feedback may be visual but integrated in a separate device, a handheld computing device or other user device communicatively linked to the ultrasound device. In still other alternative implementations, the feedback may be auditory emitted directly from the transducer housing, emitted form a secondary computing device or provided in a separate auditory input to the operator. Still other implementations may provide feedback for repositioning of the ultrasonic device through hepatic feedback indicating which direction the user may move the device to properly center the transducer to obtain optical fetal heart rate. In various embodiments, the user device may be integrated to provide, transmit, visually indicate or relay any feedback information to the operator. In still other embodiments, while in the PS Mode, the ultrasonic device may integrate all functionality therein.

Figure 2:
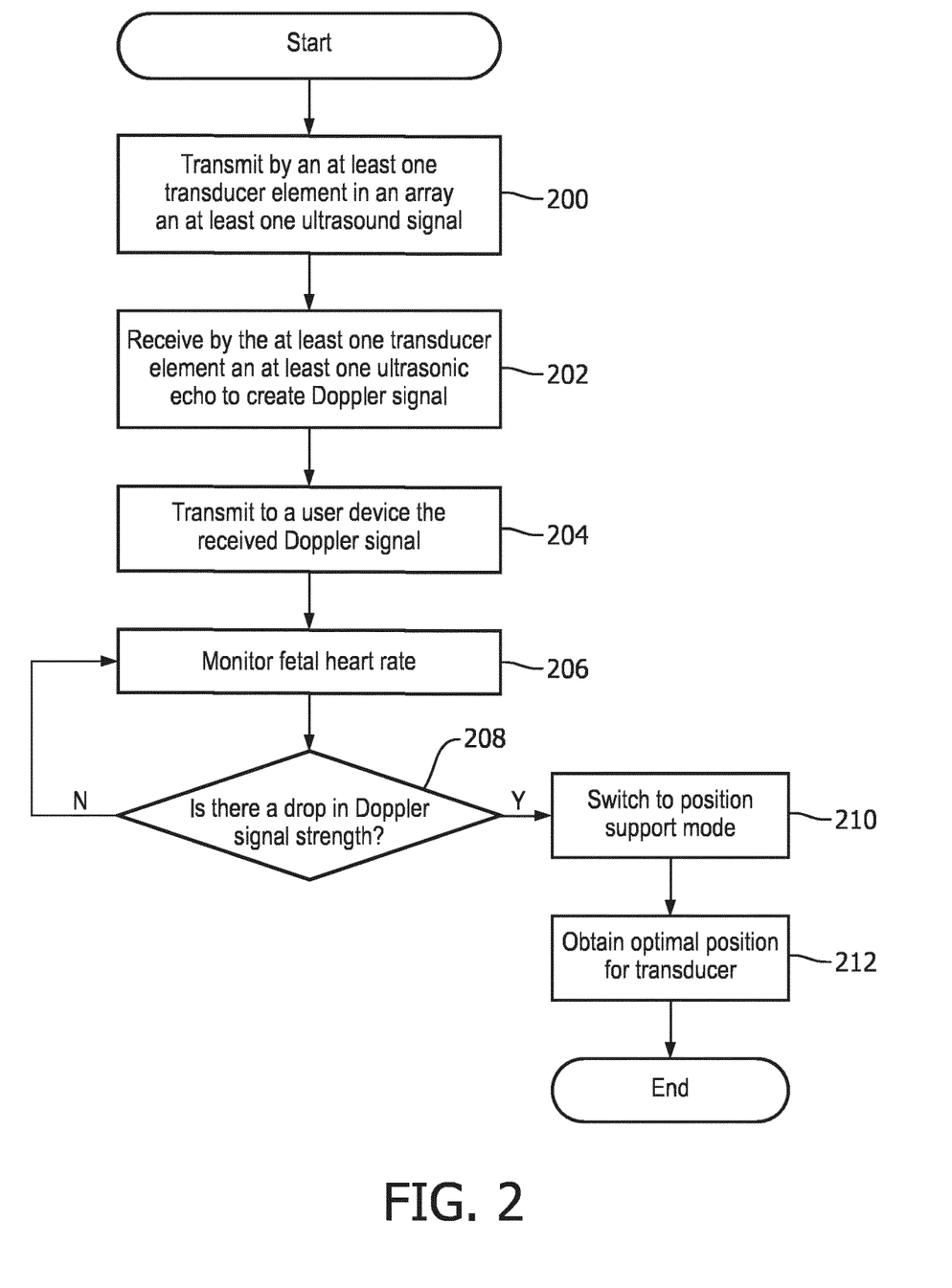
FIG. 2 is a flowchart illustrating a method for measuring a fetal heart rate, herein referred to as fetal heart rate mode (fHR-mode) of the ultrasound device, according to an embodiment of the present invention.

FIG. 2 is a flowchart illustrating a method for measuring a fetal heart rate, herein referred to as fetal heart rate mode (fHR-mode) of the ultrasound device according to another embodiment. The ultrasound device transmits an at least one ultrasound signal via an at least one transducer element in a transducer array (step 200) positioned against a maternal abdomen. The device may receive ultrasonic echoes by the at least one transducer element to create an at least one Doppler signal (step 202). Using all transmit elements for the ultrasound wave generation (such as done in fHR-mode) leads to a radiation pattern with multiple maxima. Consequently, it is difficult to link the power of the received Doppler signals unambiguously to one specific location. During the receive phase, all elements are used to receive the ultrasound echo reflected by the fetal heart. The received ultrasound echoes of each element are then preferably processed individually, and the signals may be combined via the individual receiving elements into a single channel (such as done in fHR-mode) and transmitted (step 204) via wired or wireless means to a user device.

In one embodiment, the user device processes the received Doppler signal used to monitor the fetal heart rate (step 206). While in the fHR-mode, the ultrasound device detects whether the Doppler signal strength is decreasing (step 208). In an optimal positioning of the transducer elements, the central transducer element preferably receives the strongest Doppler signal strength. In this particular example, a drop in signal strength would be detected if one of the peripheral transducer elements, instead of the central transducer element, receives the strongest Doppler signal strength. If there is no detected drop in Doppler signal strength, the ultrasound device continues monitoring the fetal heart rate (step 206). Otherwise, the ultrasound device preferably automatically switches to position support mode (210) and prompts the user to obtain an optimal position for the ultrasound device (212).

Figure 3:
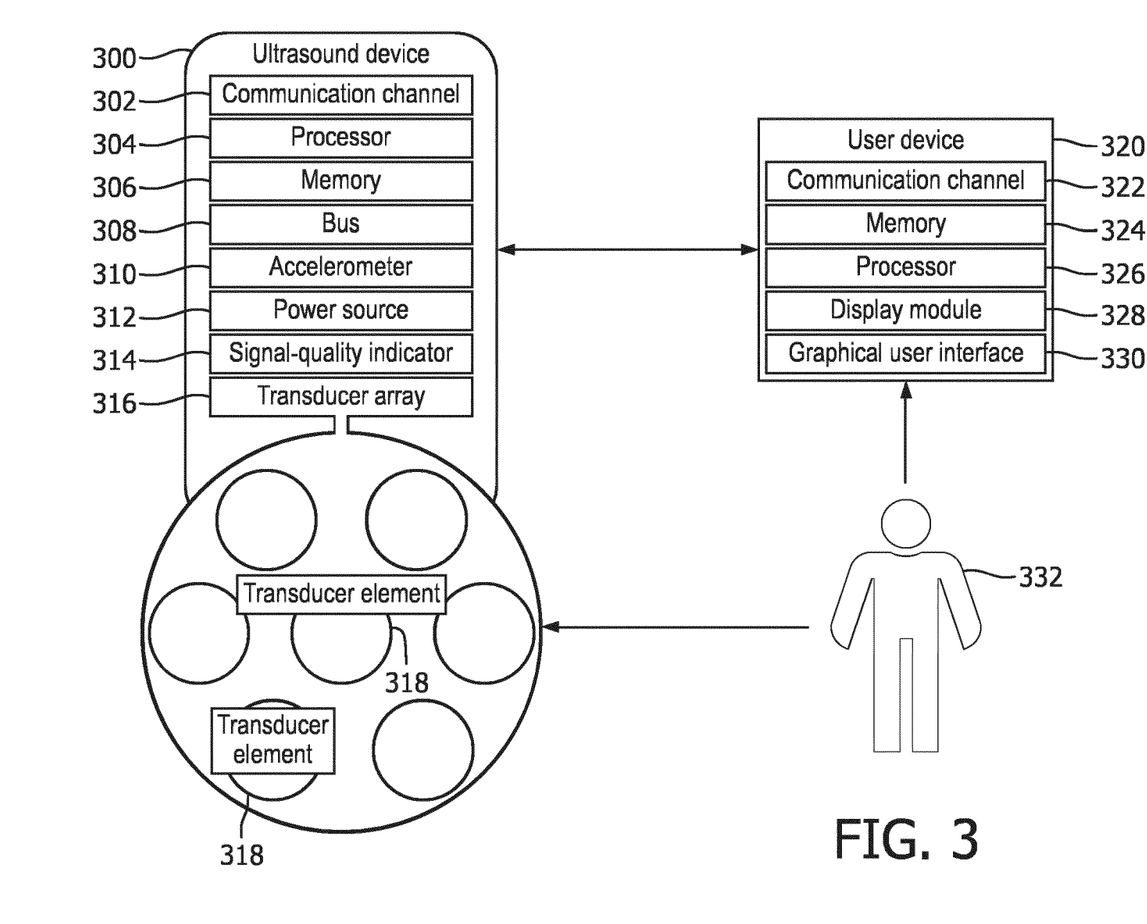
FIG. 3 illustrates a block diagram of an ultrasound device and a user device according to an embodiment of the present invention.

FIG. 3 illustrates a block diagram of an ultrasound device and a user device according to another of the multiple embodiments disclosed herein. The ultrasound device 300 comprises a communication channel 302, processor 304, memory 306, bus 308, accelerometer 310, power source 312, signal-quality indicator 314, and transducer array 316. The transducer array 316 includes at least one transducer element 318 positioned at the center of the array and a plurality of transducer elements 318 arranged in a ring around the central transducer element 318. The transducer element is preferably a piezoelectric transducer. In one embodiment, a single piezo element in the middle (not necessarily the middle one) is driven with a pulse duration (PD) of 20 cycles, a center frequency of $f_o=1$ MHz and a pulse repetition frequency of PRF=2 kHz. The PRF is typically selected from within the range of a few kHz, e.g., 3 kHz or 4 kHz. The center frequency is typically selected from within a range of $f_o=1$ MHz to 5 MHz. The pulse duration is typically selected from within a range of 5 cycles to 100 cycles. The echo signals received by the transducer elements 318 may be transmitted to the user device 320 via the communication channel 302, which can be wired cables or wireless connection means. The ultrasonic device may include all such recited elements or may include only partial structural features. Thus, the device in various embodiments may be integrated with a secondary handheld transducer array, power source or other structure such that the device is not fully integrated. Still other embodiments implement the various methods described herein on at least one of a plurality of processors that may be located on the ultrasonic device.

The user device 320 in still other embodiments may include a communication channel 322, memory 324, processor 326, display module 328, and graphical user interface (GUI) 330. The user device 320 can be any computing device such as a laptop, smartphone, or tablet. The user device may further include one of a plurality of processors to implement the various method steps and features outlined herein and may be integrated and in wired or wireless communication with the ultrasonic device 300 and may also include auditory or visual devices integrated therewith to provide feedback to the user of the measurements determined. A user 332 is able to find an optimal transducer position according to the generated multidimensional map displayed on the user device 320.

As shown in the embodiment of FIG. 3, the ultrasound device communicates with a user device 320 to display the processed Doppler signal on the display module 328 and provide feedback regarding the signal quality of the received Doppler signal. As well, a signal-quality indicator 314 on the ultrasound device 300 may provide an alert, which can be audio (e.g. beep sounds or voice alert) or visual (e.g. LED lights) in nature, to prompt the user to reposition the transducer if necessary. At least one LED light of one color is connected to at least one transducer element 318. The LED is externally installed on the ultrasound device 300. Preferably, the LED connected to the transducer receiving the strongest Doppler signal strength lights up to notify the user 332 to reposition the ultrasound device 300. If one or more peripheral transducer LED, instead of the central transducer element LED, lights up, the user 332 repositions the ultrasound device so that the central transducer receives 318 the strongest signal. If the central transducer element lights up, this indicates that the central transducer element 318 is receiving the strongest Doppler signal strength and that the ultrasound device 300 is in an optimal position.

The communications channel 302, in various implementations, enables communication between the ultrasound device 300 and an at least one user device 320. The communications channel 302 can be any transmitter or receiver used for Wi-Fi, Bluetooth, infrared, NFC, radio frequency, cellular communication, visible light communication, Li-Fi, WiMax, ZigBee, fiber optic, and other types of wireless communication devices. Alternatively, the communications channel 302 may be a physical channel such as a Universal Serial Bus (USB) cable or other wired forms of communication.

The bus 308 is a circuit that serves as a connection or interface among the aforementioned components and allows communications among them. The processor 304 may be any hardware device capable of issuing instructions, executing calculations, or processing data. As such, the processor may include a microprocessor, field programmable gate array (FPGA), application-specific integrated circuit (ASIC), or other similar devices. The processor 304 preferably receives and evaluates requests or commands from the device components and implements data processing or operation based on the evaluated requests or commands. For example, the processor 304 may calculate the fetal heart rate from the received Doppler signal. The memory 306 can either be a RAM, DRAM, ROM, and the like and may include instructions thereon which, when executed by the at least one processor 304, configures the processor to implement the various aspects noted herein.

In some implementations, a GUI 330 in the user device 320 may include one or more devices for enabling communication with a user. For example, the GUI 330 may include an interactive display, a mouse, a keyboard, buttons, camera, microphone, vibrator, haptic engine, etc. The power source 312 may be any rechargeable battery or solar battery for meeting the power requirements of the ultrasound device 300. The battery preferably can be charged using both wired and wireless charging methods.

Figure 4:
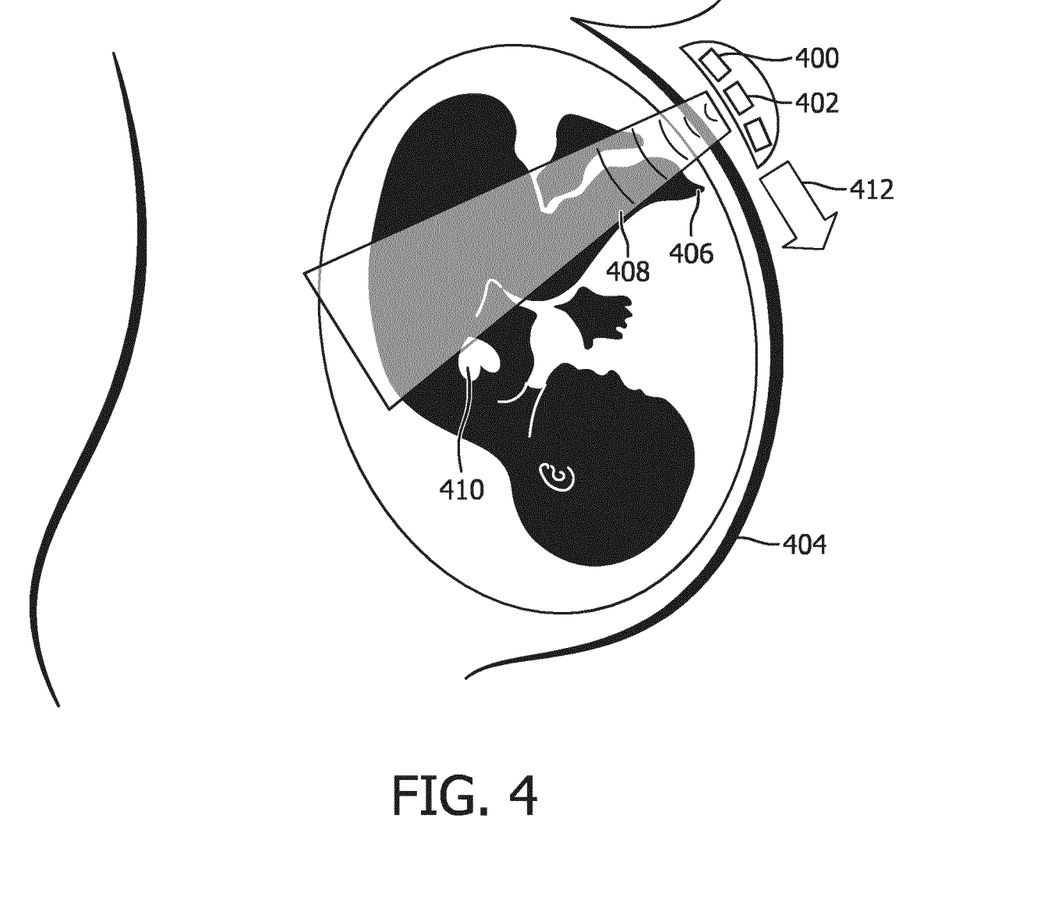
FIG. 4 shows a method for repositioning the ultrasound device to locate a fetal heart using PS-mode according to an embodiment of the present invention.

FIG. 4 discloses an embodiment of a method for repositioning the ultrasound device to locate a fetal heart using PS-mode. An ultrasound device 400, which is shown in cross-sectional view, includes transducer elements 402, which are positioned against the maternal abdomen 404. In the PS-mode, the central transducer element 402 transmits an ultrasound signal 406 that covers a beam measurement volume 408. After processing the received Doppler signal and generating a 2D-heat map, it is determined that the fetal heart 410 is not at the center of 2D-heat map or in substantial central alignment of the beam measurement volume. Feedback is then provided to the user indicating a direction of proper centrality for the fetal heart. A user then repositions the ultrasound device 400 in the direction 412 to obtain an optimal fetal heart position 410.

Figure 5:
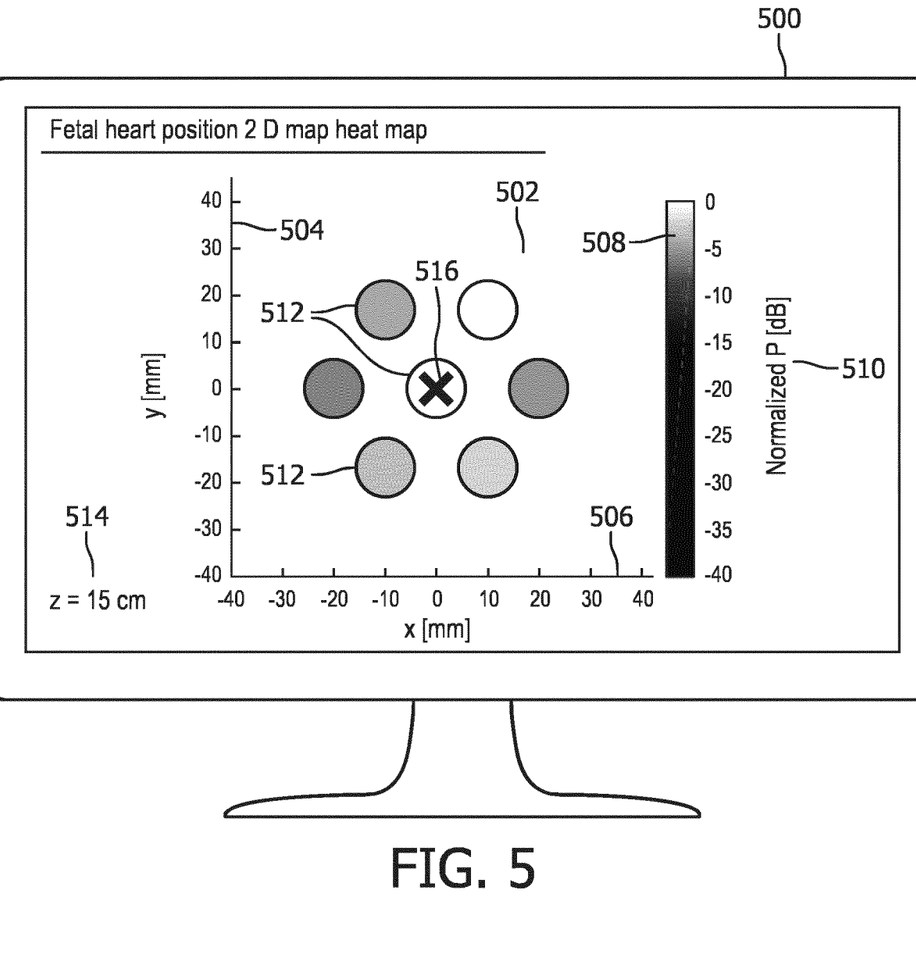
FIG. 5 shows a screenshot of a user device graphical user interface (GUI) showing a two dimensional heat map (2D- heat map) when the ultrasound transducer is in an optimal position according to an embodiment of the present invention.

FIG. 5 shows a screenshot of a user device GUI showing a 2D-heat map when the ultrasound transducer is in an optimal position according to one embodiment. As shown, the user device is a computer or associated computing device having a user interface and associated at least one processor. The GUI screen 500 shows a 2D-heat map 502. The 2D-heat map 502 including a y-axis 504, an x-axis 506, and a color bar 508, with a color bar axis 510 indicating values ranging from zero to −40 dB or in other examples from zero to −20 dB. In the 2D-heat map 502, the position of the signal received at the maternal abdomen surface in contact with the transducer elements is represented by the x-value along the x-axis 506 and a y-value along the y-axis 504 in the x-y plane. The Doppler signal strength is represented by a color value (corresponding to the Doppler signal strength for a given z-value along the color bar axis 510) represented by a point along the z-axis. The processed Doppler signal received from each transducer elements is displayed on mapped areas 512. At depth 514, each mapped area 512 contains the various Doppler signal strength values detected by each of the corresponding transducer elements. The 2D-heat map 502 also shows a central mapped area 512 assigned the lightest color in the 2D-heat map 502, which corresponds to the case where the actual position of the fetal heart, marked by the position marker 516, lies directly underneath the central transducer element.

Figure 6:
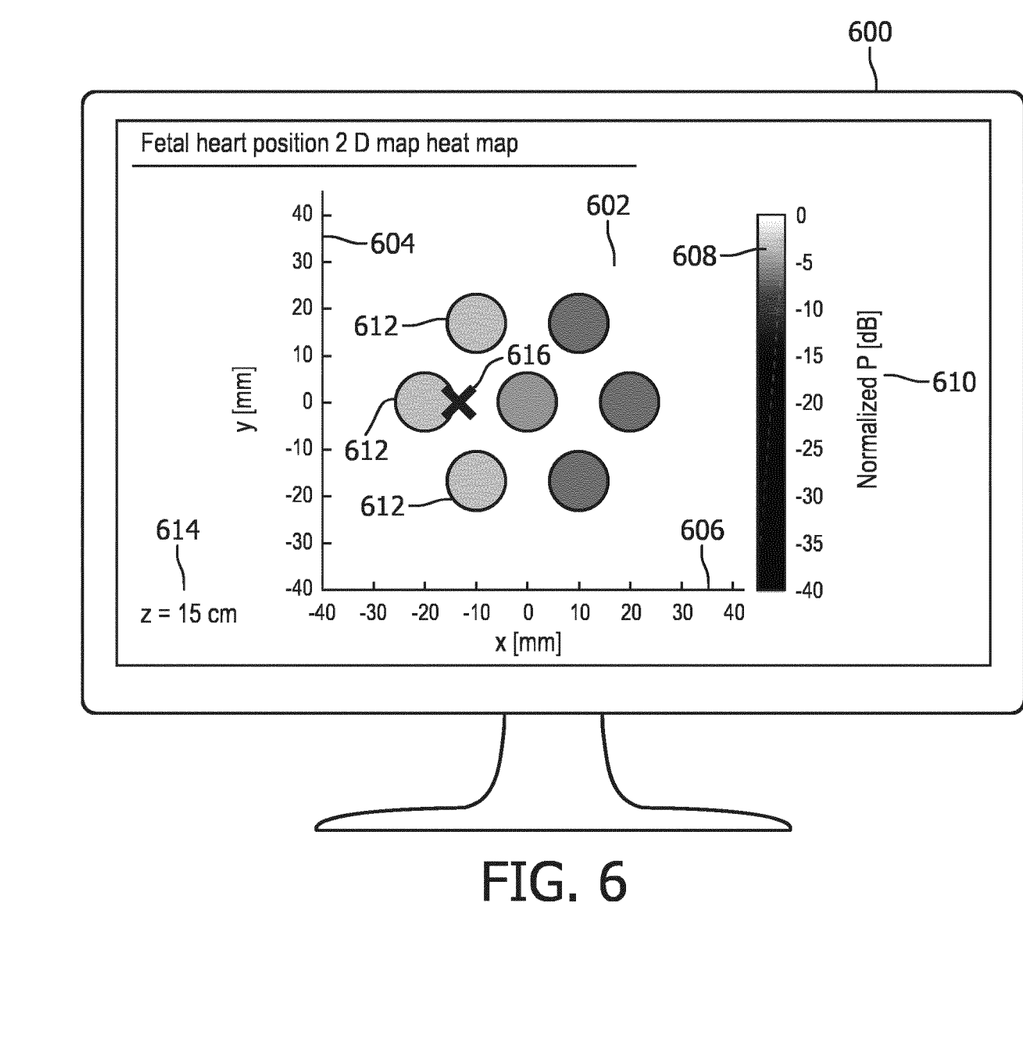
FIG. 6 is another screenshot of a user device GUI showing a 2D-heat map in a case where the ultrasound device is not positioned optimally according to an embodiment of the present invention.

FIG. 6 is another screenshot of a user device GUI showing a 2D-heat map in a case where the ultrasound device is not positioned optimally according to one embodiment. In this embodiment, the GUI screen 600 shows a 2D-heat map 602. The 2D-heat map 602 shows a y-axis 604, an x-axis 606, a color bar 608 on the right side of the figure, with a color bar axis 610 indicating values ranging from zero to −40 dB. In the 2D-heat map 602, the position of the Doppler signal received at the maternal abdomen in contact with the transducer elements corresponds to an x-value along the x-axis 606 and a y-value along the y-axis 604 in the x-y plane. A Doppler signal strength is assigned a corresponding color as shown on the color bar axis 610. The processed Doppler signals received from the transducer elements is displayed on each of the seven mapped areas 612. In FIG. 6, each mapped area 612 corresponds to one transducer element. At depth 614, the 2D-heat map 602 shows that the transducer for the mapped peripheral area 612 has detected strong Doppler signals, which can be seen from the mapped area's light color shading compared with those of the other mapped areas. This means that the actual position of the fetal heart, marked by the position marker 616, lies not at a centralized location where the radiation pattern has its maximum, generally in front of the central element and substantially centralized over the measurement volume, but at a location just outside the area scanned by the central transducer element. When the fetal heart position lies completely outside the measurement volume 408, no information on the fetal heart location can be obtained or determined.

Figure 7:
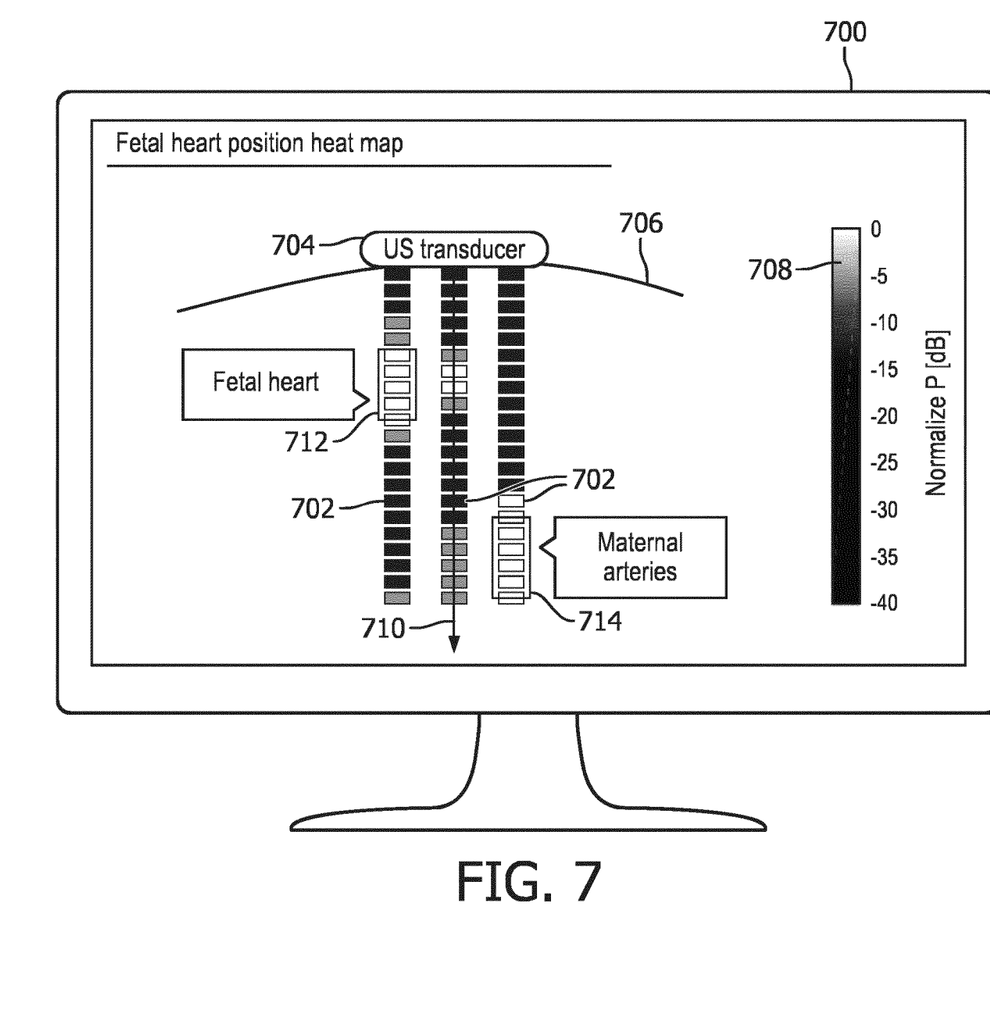
FIG. 7 shows a screenshot of a user device GUI according to an embodiment of the invention that depicts a heat map comprising segmented heat maps each of which represents detected Doppler signals having strengths that vary depending on the distance between the maternal abdomen surface and the fetal heart.

FIG. 7 shows a screenshot of a user device GUI 700 according to another implementation which depicts a heat map comprising segmented heat maps 702 each of which represents detected Doppler signals having strengths that vary depending on the distance between the maternal abdomen surface and the fetal heart. In this embodiment, the segmented heat maps 702 are generated from Doppler signals that emanate from the fetal heart and detected maternal arteries. FIG. 7 also shows an ultrasound transducer 704, a maternal abdomen surface 706, three segmented heat maps 702 in which the axis along the length of each segmented heat map represents the z-axis, and a color bar 708. Each of the segmented heat maps 702 represents a mapping of the processed Doppler signal strength received from at least one transducer element that corresponds to a given distance range between the maternal abdomen and the fetal heart. FIG. 7 shows, but is not limited to, three segmented heat maps 702 extending along the longitudinal transducer axis 710. Here, the ultrasound transducer 706 lies in a first position where two hot spot regions 712 and 714 (light-colored regions corresponding to strong Doppler signal strengths from the fetal heart and maternal arteries, respectively) are shown on the segmented heat maps 702.

Figure 8:
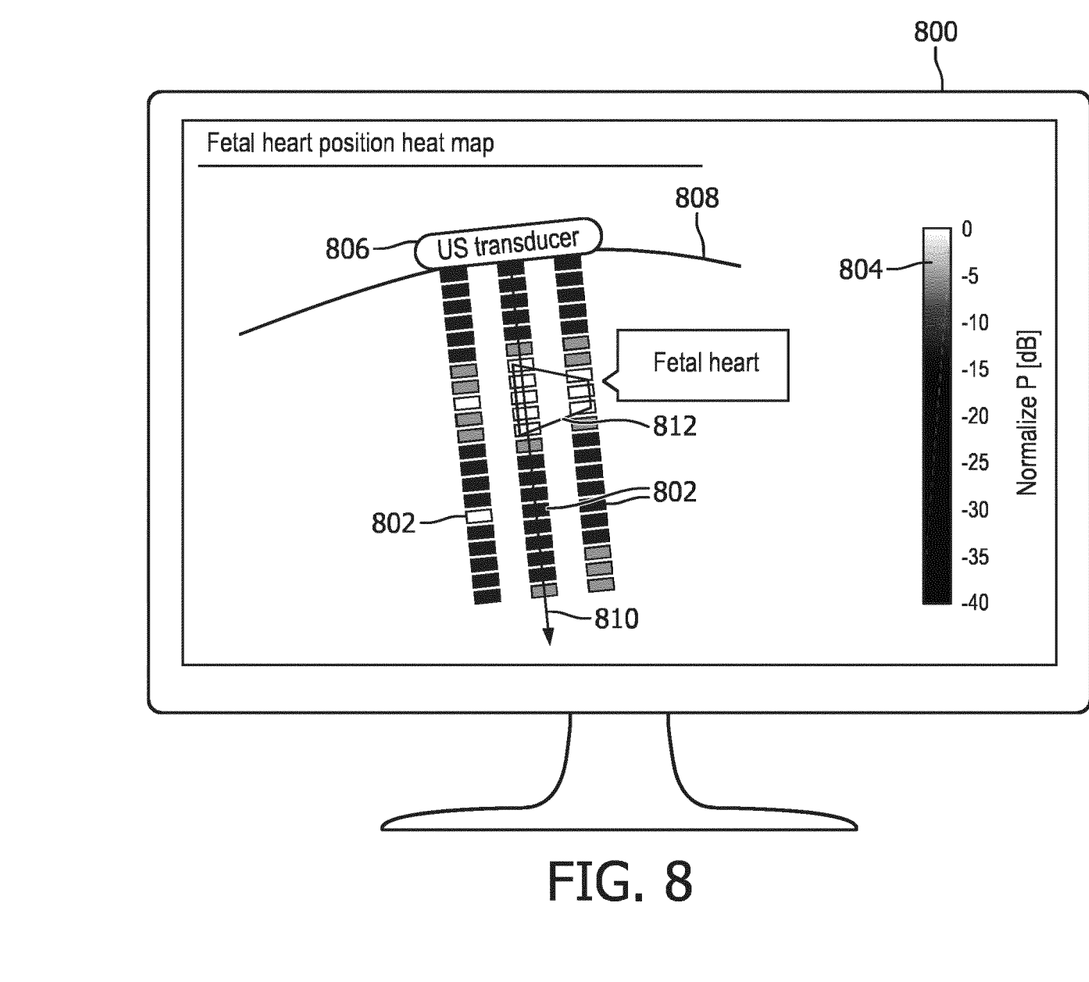
FIG. 8 shows a screenshot of a user device GUI showing a heat map when the ultrasound device is repositioned to exclude detection of the maternal arteries from the measurement volume and detect only signal from the fetal heart according to an embodiment of the present invention.

FIG. 8 shows a screenshot of a user device GUI showing a heat map when the ultrasound device is repositioned to exclude detection of the maternal arteries from the measurement volume and detect only signal from the fetal heart. FIG. 8 shows a GUI screen 800, three segmented heat maps 802 in which the axis along the length of each segmented heat map represents the z-axis, a color bar 804, an ultrasound transducer 806, and a maternal abdomen surface 808. In this example, the segmented heat maps 802 are generated from Doppler signals that include signals from the fetal heart. Each of the segmented heat maps 802 represents a mapping of the processed Doppler signal strength (received from at least one transducer element) that varies according to a given distance range (represented by a segment or slice of the bar) between the maternal abdomen and the fetal heart. FIG. 8 shows, but is not limited to, three segmented heat maps 802 extending along the longitudinal transducer axis 810. Here, the ultrasound transducer 806 is shown in a second position relative to the first position described in FIG. 7, where only one hotspot 812 (i.e., strong signal coming from only one source, in this case, the fetal heart) is detected in the segmented heat maps 802. In one example, when an obstetrician wants to start a fHR recording or when the fHR signal is lost and the US-transducer needs to be repositioned, the PS-mode can be activated to obtain visual feedback. For optimal transducer positioning, the fetal heart should be centered below the middle element, since this will minimize the chance that the fetal heart is moving out of the ultrasound beam. When the optimal position is found the device preferably switches back to the fHR-mode.

While operating in fHR-mode, in fixed time intervals the device is preferably switched into the PS-mode to obtain fetal heart location information. When the fetal heart is slowly drifting out of the ultrasonic beam, a different element will receive the strongest Doppler signal. The direction of this displacement can be detected and feedback can be given, to avoid signal loss. In some embodiments, such movement direction of the fetal heart may be stored and provided as feedback, upon request, to an operator who may be repositioning the device. By providing information related to direction of movement of the heart, it may be easier to reposition the transducer and locating the fetal heart.

Accelerometers in the ultrasound transducer may also be utilized to detect when the ultrasound transducer has suddenly moved. In such an instance, in some embodiments, the transducer may automatically switch to the PS-mode. Other embodiments may be implemented for detection of transducer movement such as capacitive sensors, infrared sensors, etc., which detect when the transducer is misplaced and the PS-mode needs to be activated. Alternatively, the fUR can also be measured during the PS-mode. When the fetal heart has moved out of the measurement volume, the fHR-mode can be activated to obtain a Doppler signal from a larger measurement volume.

In yet another embodiment, the transmitted Doppler signal strengths are used to generate a 3D heat map. The Doppler signal is strongest from moving objects, such as a fetal heart or maternal arteries. Preferably, the Doppler signal strength is measured in decibels (dB). From the received ultrasound echoes, the Doppler signal is calculated for a selected sample volume. Every object moving within this sample volume contributes to the received Doppler signal. The start $z_{start}$ of the sample volume, the end $z_{end}$ of the sample volume and the sample volume length SVL are given by $$SVL = z_{end} - z_{start} = \frac{c_0(T + \Delta\tau)}{2}; \quad (1)$$

$$z_{start} = \frac{c_0(\tau_s - T)}{2}; \quad (2)$$

$$z_{end} = \frac{c_0(\tau_s + \Delta\tau)}{2} \quad (3)$$

With $c_0$ the speed of sound, $\tau_s$ the time till the opening of the range gate, $\Delta\tau$ the range gate duration and T the length of the pulse. By using multiple range gates the Doppler signal from different depths/sample volumes can be obtained. The x-y localization of the fetal heart can thus be done for different depths z. In this embodiment, the power of the Doppler signal from different depths can be calculated. This allows generation of a coarse 3D-heat map of Doppler sources in the maternal abdomen, i.e., one could for example generate images for different range gates. The 2D depth map shown in FIGS. 7 and 8 may, in various embodiments, be the cross section of the coarse 3D-heat map, showing the Doppler signal strength from different sample measurement volume for three different transducer elements.

With this 3D visualization of Doppler power, one can identify the location of different Doppler sources in the maternal abdomen. When the maternal heart rate is measured externally it can be distinguished from fetal heart rate. A pulsating maternal artery could therefore be annotated in the 3D-heat map. This in turn can provide feedback to a clinician on how the transducer should be moved to exclude the maternal artery from the measurement volume.

The ultrasound device or the user device typically includes at least one processor which may communicate with peripheral devices. These peripheral devices may include a memory or storage subsystems as described herein, including, for example, a memory subsystem and a file storage subsystem, user interface output devices, user interface input devices, and communication interfaces. The input and output devices allow user interaction with any of the devices and/or other computing devices. Communication interfaces provides an interface to outside networks and is coupled to corresponding devices in other computing devices.

The implementation of the various visualizations and user interactions may be completed by software modules stored in memory. The software modules may be stored in memory of the ultrasonic device, a user device or another storage subsystem for maintaining the programs. A storage subsystem stores programming and data constructs that provide the functionality of some or all of the modules and/or methods described herein. For example, a storage subsystem may be provided to include the logic to perform selected aspects of the method of FIGS. 1-2 and/or implement the various user interfaces. These software modules are generally executed by processors alone or in combination with other processors. Memory used in the described system and/or in a storage subsystem can include a number of memories including a main random access memory (RAM) for storage of instructions and data during program execution and a read only memory (ROM) in which fixed instructions are stored. A file storage subsystem can also provide persistent storage for programs and data files, and may include a hard disk drive, a floppy disk drive along with associated removable media, a CD-ROM drive, an optical drive, or removable media cartridges. The modules implementing the functionality of certain implementations may be stored by file storage subsystem in the storage subsystem, or in other machines or devices accessible by the processor(s) of the ultrasound device, user device or alternative device.

The user device may include a user interface input which may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" or "User Device" is intended to include all possible types of devices and ways to provide information to a user, input information into computing device or onto a communication network. The User Device may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image or other information. The display subsystem may also provide non-visual display such as via audio output devices. In general, use of the term "output device" or User Device or GUI is intended to include all possible types of devices and ways to output information from User Device or Ultrasonic Device to the user or to another machine or computing device.

In various embodiments, when measuring twins, possibly two Doppler sources are identifiable within the maternal abdomen. This feedback could be used to position the transducer in a way that the two fetal hearts are clearly separated in space and do not fall into the same volume of observation.

In various embodiments, the 2D-heat map can be integrated with the depth heat map to form a volumetric 3D heat map defined by three orthogonal axes, x, y and z. In another embodiment of the present disclosure, the 2D-heat map can be displayed side-by-side, in one window of the computer, with the depth map, in another window of the computer. While viewing the 2D-heat map, the depth heat map may display a highlighted portion of the depth with which the 2D-heat map is being viewed.

In yet another embodiment, the pregnant woman may also choose to wirelessly connect her tablet supporting a software that is able to display the heat map to the ultrasound device to view the generated heat map. The medical personnel uses the heat map to obtain an optimal position of the fetal heart.

The device and methods disclosed herein may be used for hospital and home monitoring of fetal heart rate, for example, during labor and delivery.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The invention claimed is:

1. A method of monitoring fetal health, comprising:
   transmitting an ultrasound signal from at least one transducer element in an array towards a maternal abdomen to create a measurement volume;
   receiving by the at least one transducer element at least one ultrasound signal echo corresponding to at least one depth of the maternal abdomen;
   processing in at least one channel the at least one ultrasound signal echo received by the at least one transducer element to create at least one Doppler signal;
   generating a multidimensional heat map from the at least one Doppler signal;
   determining from the multidimensional heat map whether a fetal heart lies outside a central alignment of the measurement volume;
   providing feedback on how to reposition the at least one transducer element, such that the fetal heart lies within the central alignment of the measurement volume, when the fetal heart is determined to lie outside the central alignment of the measurement volume; and
   automatically entering a fetal heart rate monitoring mode upon determining that the fetal heart lies within the central alignment of the measurement volume.

2. The method of monitoring fetal health of claim 1, wherein generating the multidimensional heat map from the at least one Doppler signal includes generating a two-dimensional (2D) heat map integrated with a depth heat map.

3. The method of monitoring fetal health of claim 1, further comprising automatically switching from the fetal heart rate monitoring mode to a position support mode when the fetal heart is determined to lie outside the central alignment of the measurement volume.

4. The method of monitoring fetal health of claim 1, wherein generating the multidimensional heat map from the pat least one Doppler signal includes generating a two-dimensional (2D) map and a depth heat map, and presenting both the 2D heat map and the depth heat map on a user device.

5. The method of monitoring fetal health of claim 4, further comprising highlighting a portion of the depth heat map corresponding to a portion of the 2D heat map being displayed.

6. The method of monitoring fetal health of claim 1, wherein generating the multidimensional heat map from the at least one Doppler signal includes generating a three-dimensional (3D) heat map.

7. The method of monitoring fetal health of claim 6, wherein generating the 3D heat map includes measuring a plurality of Doppler signals at a plurality of sample volumes.

8. The method of monitoring fetal health of claim 7, wherein measuring of the plurality of Doppler signals includes using a plurality of range gates.

9. The method of monitoring fetal health of claim 1, further comprising determining a direction towards the fetal heart.

10. The method of monitoring fetal health of claim 9, wherein providing the feedback includes transmitting haptic feedback through an ultrasound device.

11. The method of monitoring fetal health of claim 9, wherein providing the feedback includes providing a directional indication towards the fetal heart based on the determined direction towards the fetal heart.

12. The method of monitoring fetal health of claim 11, wherein providing the feedback includes illuminating an LED on a housing associated with the at least one transducer element.

13. The method of monitoring fetal health of claim 11, wherein providing the feedback includes providing visual feedback of the directional indication on a user device.

14. A method of monitoring fetal health, comprising:
   entering a position support mode of operation for an ultrasound device;
   transmitting ultrasound signals from at least one transducer of the ultrasound device to create a measurement volume;
   receiving by the at least one transducer ultrasound signal echoes corresponding to depth in a maternal abdomen;
   processing by a processor the received ultrasound signal echoes received by the at least one transducer to create at least one Doppler signal;
   generating a multi-dimensional heat map from the at least one Doppler signal;
   determining from the multi-dimensional heat map, when a fetal heart is outside a central alignment of the measurement volume;
   providing feedback on how to reposition the at least one transducer such that the fetal heart lies within the central alignment of the measurement volume when the fetal heart is determined to be outside the central alignment of the measurement volume; and
   automatically entering a fetal heart rate monitoring mode upon determining that the fetal heart lies within the central alignment of the measurements volume.

15. The method of claim 14, wherein providing the feedback includes presenting information on a user device indicating a direction from a center of the measurement volume.

16. The method of claim 14, further comprising switching the ultrasound device from the fetal heart rate monitoring mode to the position support mode of operation upon detecting when the fetal heart lies outside the central alignment of the measurement volume.

17. The method of claim 14, wherein the multi-dimensional heat map is a combined construct of a two dimensional heat map and a depth heat map.

18. The method of claim 14, wherein providing the feedback includes illuminating at least one light source on the ultrasound device.

19. The method of claim 18, wherein the at least one light source indicates a direction from a center of the measurement volume towards the fetal heart.

20. An apparatus for monitoring fetal health, comprising:
   an ultrasound device having a plurality of transducers;
   at least one processor; and
   a non-transitory memory storing instructions which, when executed by the at least one processor, cause the at least one processor to:
   transmit ultrasound signals from the plurality of transducers of the ultrasound device;
   receive by the plurality of transducers ultrasound signal echoes corresponding to depth in a maternal abdomen;
   create Doppler signals based upon the ultrasound signal echoes received by the plurality of transducers;
   generate a multi-dimensional heat map from the Doppler signals;
   determine from the multi-dimensional heat map when a fetal heart lies outside a central alignment of a measurement volume;
   provide directional feedback on how to reposition the ultrasound device such that the fetal heart lies within the central alignment of the measurement volume when the fetal heart is determined to lie outside the central alignment of the measurement volume; and
   automatically entering a fetal heart monitoring mode upon determining that the fetal heart lies within the central alignment of the measurements volume.

* * * * *